United States Patent
Ohtsuka et al.

(10) Patent No.: US 9,388,117 B2
(45) Date of Patent: Jul. 12, 2016

(54) METHOD FOR PRODUCING α-FLUOROACRYLIC ACID ESTER

(71) Applicant: DAIKIN INDUSTRIES, LTD., Osaka (JP)

(72) Inventors: Tatsuya Ohtsuka, Osaka (JP); Akihiro Gotou, Osaka (JP); Sumi Ishihara, Osaka (JP); Yoshihiro Yamamoto, Osaka (JP); Akinori Yamamoto, Osaka (JP); Yoshichika Kuroki, Osaka (JP); Yuzo Komatsu, Osaka (JP); Yousuke Kishikawa, Osaka (JP)

(73) Assignee: DAIKIN INDUSTRIES, LTD., Osaka (JP)

( * ) Notice: Subject to any disclaimer, the term of this patent is extended or adjusted under 35 U.S.C. 154(b) by 0 days.

(21) Appl. No.: 14/420,924

(22) PCT Filed: Aug. 30, 2013

(86) PCT No.: PCT/JP2013/073446
§ 371 (c)(1),
(2) Date: Feb. 11, 2015

(87) PCT Pub. No.: WO2014/034906
PCT Pub. Date: Mar. 6, 2014

(65) Prior Publication Data
US 2015/0191413 A1    Jul. 9, 2015

(30) Foreign Application Priority Data
Aug. 30, 2012  (JP) .................. 2012-189855

(51) Int. Cl.
*C07C 67/36* (2006.01)
*B01J 31/02* (2006.01)
*B01J 31/24* (2006.01)

(52) U.S. Cl.
CPC ............. *C07C 67/36* (2013.01); *B01J 31/0237* (2013.01); *B01J 31/24* (2013.01); *B01J 31/2404* (2013.01); *B01J 31/2409* (2013.01); *B01J 2231/321* (2013.01); *B01J 2531/824* (2013.01)

(58) Field of Classification Search
CPC .................................................... C07C 67/36
See application file for complete search history.

(56) References Cited

U.S. PATENT DOCUMENTS 3,988,358 A * 10/1976 Heck .............................. 558/353
5,231,219 A    7/1993 Grison et al.

FOREIGN PATENT DOCUMENTS

| JP | 58-154529 | 9/1983 |
| JP | 60-158136 | 8/1985 |
| JP | 5-201921  | 8/1993 |
| JP | 2006-8636 | 1/2006 |

OTHER PUBLICATIONS

Xu et al. Journal of Organic Chemistry, 2005, 70, p. 4346-4353.*
International Search Report issued Dec. 3, 2013 in International (PCT) Application No. PCT/JP2013/073446.
Schoenberg et al., "Palladium-Catalyzed Carboalkoxylation of Aryl, Benzyl, and Vinylic Halides", J. Org. Chem., vol. 39, No. 23, 1974, pp. 3318-3326.
Extended European Search Report issued Mar. 18, 2016 in corresponding European Application No. 13833707.6.
Wesolowski et al., "Palladium-Catalyzed Stereospecific Carboalkoxylation of 1,2-Difluoro-1-iodoalkenes and α,β-Difluoro-β-iodostyrenes", Tetrahedron Letters, vol. 40, No. 12, 1999, pp. 2243-2246.

* cited by examiner

*Primary Examiner* — Yong Chu
(74) *Attorney, Agent, or Firm* — Wenderoth, Lind & Ponack, L.L.P.

(57) ABSTRACT

The object of the present invention is to provide a process for producing α-fluoroacrylic acid ester at a high starting material conversion, high selectivity, and high yield. The present invention provides a process for producing the compound represented by the formula (1) wherein R represents alkyl optionally substituted with one or more fluorine atoms, the process comprising step A of reacting a compound represented by the formula (2) wherein X represents a bromine atom or a chlorine atom with an alcohol represented by the formula (3) wherein the symbol is as defined above, and carbon monoxide in the presence of a transition metal catalyst and a base to thereby obtain the compound represented by the formula (1).

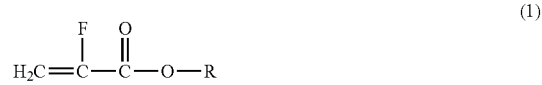

(1)

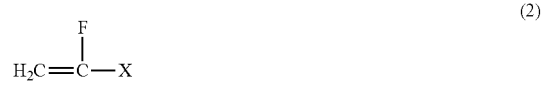

(2)

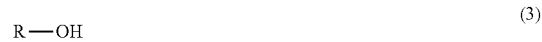

(3)

4 Claims, No Drawings

METHOD FOR PRODUCING α-FLUOROACRYLIC ACID ESTER

TECHNICAL FIELD

The present invention relates to a process for producing α-fluoroacrylic acid ester.

BACKGROUND ART

α-Fluoroacrylic acid ester is useful, for example, as a synthetic intermediate for medical drugs (e.g., antibiotic drugs), a synthetic intermediate for cladding materials of optical fibers, a synthetic intermediate for painting materials, a synthetic intermediate for semiconductor resist materials, and a monomer for functional polymers. Examples of conventional processes for producing α-fluoroacrylic acid ester in an excellent yield include the process proposed in Patent Document 1 for producing α-fluoroacrylic acid ester by subjecting α-fluorophosphono acetate and paraformaldehyde to a condensation reaction, the process being characterized in that the condensation reaction is carried out in an aqueous medium in the presence of a weak inorganic base.

CITATION LIST

Patent Document

Patent Document 1: JPH05-201921A

SUMMARY OF INVENTION

Technical Problem

The yield of α-fluoroacrylic acid ester according to the process disclosed in Patent Document 1, however, is 82% at most, and a process for achieving a higher yield is desired. In particular, it is desirable that synthetic intermediates, for example, for producing medical drugs, contain by-products in an extremely low amount from the standpoint of medical drug safety; thus, a high selectivity of α-fluoroacrylic acid ester is required. Nonetheless, in the conventional processes for producing 2-fluoroacrylic acid, the reaction is typically complicated because of the generation of derivatives or so on; the yield of 2-fluoroacrylic acid is low; and the separation of 2-fluoroacrylic acid is difficult. Therefore, conventional processes have a disadvantage in industrial application in that by-products must be removed to increase the purity of 2-fluoroacrylic acid, whereby large amounts of waste fluids and waste materials are produced. Accordingly, an object of the present invention is to provide a process for producing α-fluoroacrylic acid ester at a high starting material conversion, high selectivity, and high yield.

Solution to Problem

The present inventors found that a compound, which is α-fluoroacrylic acid ester, represented by the formula (1)

(1)

wherein R represents alkyl optionally substituted with one or more fluorine atoms, is obtained at a high starting material conversion, high selectivity, and high yield by reacting a compound represented by the formula (2)

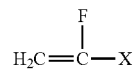
(2)

wherein X represents a bromine atom or a chlorine atom with an alcohol represented by the formula (3)

  (3)

wherein the symbol is as defined above and carbon monoxide in the presence of a transition metal catalyst and a base, and the inventors completed the invention.

Specifically, the present invention includes the aspects presented in the following items.

Item 1.

A process for producing a compound represented by the formula (1)

(1)

wherein R represents alkyl optionally substituted with one or more fluorine atoms,
the process comprising step A of reacting a compound represented by the formula (2)

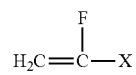
(2)

wherein X represents a bromine atom or a chlorine atom with an alcohol represented by the formula (3)

  (3)

wherein the symbol is as defined above and carbon monoxide in the presence of a transition metal catalyst and a base to thereby obtain the compound represented by the formula (1).

Item 2. The process according to Item 1, wherein the transition metal catalyst is a palladium catalyst.

Item 3. The process according to Item 1 or 2, wherein the base comprises an amine and an inorganic base.

Item 4. The process according to any one of Items 1 to 3, wherein step A is carried out at a temperature ranging from 60 to 120° C.

Advantageous Effects of Invention

The process according to the present invention enables production of α-fluoroacrylic acid ester at a high starting material conversion, high selectivity, and high yield.

DESCRIPTION OF EMBODIMENTS

In this specification, examples of alkyl groups include $C_{1-6}$ alkyl group, such as methyl group, ethyl group, propyl group, isopropyl group, butyl group, isobutyl group, sec-butyl group, tert-butyl group, pentyl group, neopentyl group, and hexyl group.

In this specification, examples of cycloalkyl groups include $C_{3-8}$ cycloalkyl groups, such as cyclopentyl group, cyclohexyl group, and cycloheptyl group.

In this specification, the term "(cyclo)alkyl group" is intended to include alkyl groups and cycloalkyl groups.

A process according to the present invention for producing a compound represented by the formula (1)

  (1)

wherein R represents alkyl optionally substituted with one or more fluorine atoms, comprises step A of reacting a compound represented by the formula (2)

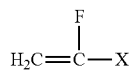  (2)

wherein X represents a bromine atom or a chlorine atom with an alcohol represented by the formula (3)

R—OH  (3)

wherein the symbol is as defined above and carbon monoxide in the presence of a transition metal catalyst and a base to thereby obtain the compound represented by the formula (1).

The alkyl group of the "alkyl optionally substituted with one or more fluorine atoms" represented by R is preferably methyl group or ethyl group, and particularly preferably methyl group.

The compound represented by the formula (1) is preferably methyl 2-fluoroacrylate or ethyl 2-fluoroacrylate, and particularly preferably methyl 2-fluoroacrylate.

The compound represented by the formula (2) is a known compound, which can be produced in accordance with a known procedure, and is also commercially available.

The alcohol represented by the formula (3) is preferably methanol or ethanol, and particularly preferably methanol. The alcohol represented by the formula (3) can also serve as a solvent for the reaction of step A. The amount of the alcohol represented by the formula (3) as a reactant of step A is typically in the range of 1 to 100 moles, and preferably in the range of about 1.2 to 40 moles per mole of the compound represented by the formula (2). When used as a reaction solvent of step A, the alcohol represented by the formula (3) is used typically in an excessive amount with respect to the amount of the compound represented by the formula (2). Specifically, when no solvents other than the alcohol is used, the amount of the alcohol is in the range of 0.2 to 10 L, preferably in the range of about 0.4 to 5 L or in the range of 0.5 to 10 L, or in the range of about 1 to 5 L, per mole of the compound represented by the formula (2).

Step A is preferably carried out in a container such as an autoclave, and the carbon monoxide used as a reactant of step A can be introduced into the container by using a carbon monoxide-containing gas, such as purified carbon monoxide gas. The pressure of the carbon monoxide is typically 0.1 to 10 MPaG, and preferably 0.5 to 2 MPaG.

Step A is carried out in the presence of a transition metal catalyst. Examples of transition metal catalysts used in step A include those containing one or more kinds of transition metals selected from the group consisting of nickel, palladium, platinum, rhodium, ruthenium, iridium, and cobalt. In other words, examples of transition metal catalysts used in step A include nickel catalysts, palladium catalysts, platinum catalysts, rhodium catalysts, ruthenium catalysts, iridium catalysts, and cobalt catalysts. The transition metal is preferably selected from the group consisting of nickel, cobalt, and palladium. In a preferred embodiment of the present invention, examples of the transition metal catalyst containing one or more kinds of transition metals selected from the group consisting of nickel, cobalt, and palladium include organic nickel complexes, organic cobalt complexes, and organic palladium complexes.

The nickel complexes, the cobalt complexes, and the palladium complexes refer to either complexes added as a reagent or complexes generated in a reaction system.

Examples of palladium complexes include zerovalent palladium complexes; zerovalent palladium complexes generated from divalent palladium complexes during a reaction; and complexes obtained by mixing these palladium complexes with at least one compound (ligand) selected from the group consisting of diketones, phosphines, diamines, and bipyridyls.

Examples of zerovalent palladium complexes include, but are not particularly limited to, $Pd_2(DBA)_3$ (DBA is dibenzylideneacetone), $Pd(COD)_2$ (COD is cycloocta-1,5-diene), $Pd(DPPE)$ (DPPE is 1,2-bisdiphenylphosphinoethane), $Pd(PCy_3)_2$ (Cy is cyclohexyl), $Pd(Pt-Bu_3)_2$ (t-Bu is t-butyl), and $Pd(PPh_3)_4$ (Ph is phenyl).

Examples of divalent palladium complexes include palladium chloride, palladium bromide, palladium acetate, bis (acetylacetonato)palladium(II), dichloro($\eta^4$-1,5-cyclooctadiene)palladium(II), and complexes obtained by binding a phosphine ligand, such as triphenyl phosphine, to these complexes. These divalent palladium complexes are, for example, reduced by a reducing species (e.g., phosphines, zinc, and organic metal reagents) that is co-present during a reaction, whereby zerovalent palladium complexes are generated.

The above-described zerovalent palladium complexes or zerovalent palladium complexes generated from divalent palladium complexes through reduction can interact with a compound (ligand), such as diketones, phosphines, diamines, and bipyridyls, that is optionally added during a reaction, and can be converted into zerovalent palladium complexes that are involved in the reaction. It is not always necessary to know how many ligands are bound to a zerovalent palladium complex during the reaction.

Using the above ligands, these palladium complexes are often formed into a homogeneous solution with a reaction substrate to be used in the reaction. In addition, these palladium complexes can also be used as a heterogeneous catalyst dispersed or supported in a polymer such as polystyrene and polyethylene. Such heterogeneous catalysts have an advantage in a process, for example, in a catalyst recovering process. Specific examples of catalyst structures include those in which a metal atom is immobilized by a polymeric phosphine that is a crosslinked polystyrene (PS) chain having a phosphine introduced therein, as shown in the following chemical formula. In addition, polymeric phosphines disclosed in the following documents can also be used.

1) Kanbara et al., Macromolecules, 2000, Volume 33, Page 657
2) Yamamoto et al., J. Polym. Sci., 2002, Volume 40, Page 2637
3) JPH06-032763A
4) JP2005-281454A
5) JP2009-527352A

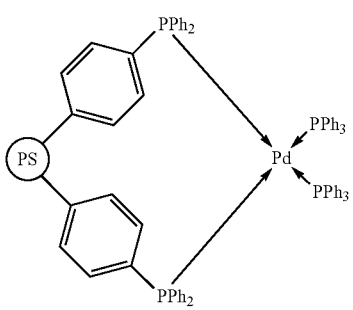

wherein PS represents polystyrene and Ph represents phenyl.

Examples of diketones include β-diketones, such as acetylacetone, 1-phenyl-1,3-butanedione, and 1,3-diphenylpropanedione.

A phosphine may have one or more substituents attached to the phosphorus atom, the substituent being selected from the group consisting of optionally substituted alkyl groups, optionally substituted cycloalkyl groups, and optionally substituted aryl groups. In particular, tri(cyclo)alkylphosphines and triarylphosphines are preferable. Specific examples of tri(cyclo)alkylphosphines include tri($C_{3-20}$ (cyclo)alkyl) phosphines, such as tricyclohexylphosphine, triisopropylphosphine, tri-t-butylphosphine, trihexylphosphine, triadamantylphosphine, tricyclopentylphosphine, di-t-butylmethylphosphine, tribicyclo[2,2,2]octylphosphine, and trinorbornylphosphine. Specific examples of triarylphosphines include tri(monocyclic aryl)phosphines, such as triphenylphosphine, trimesitylphosphine, and tri(o-tolyl)phosphine. Of these, triphenylphosphine, tricyclohexylphosphine, and tri-t-butylphosphine are preferable. In addition, the following are also useful: 2-dicyclohexylphosphino-2'4'6'-triisopropylbiphenyl, [4-(N,N-dimethylamino)phenyl]di-tert-butylphosphine, and bidentate ligands, such as 4,5-bis(diphenylphosphino)-9,9-dimethyl-9H-xanthene, 1,4-bis(diphenylphosphino)butane, 1,3-bis(diphenylphosphino) propane, 1,1'-bis(diphenylphosphino)ferrocene, and 2,2'-bis(diphenylphosphino)-1,1'-binaphthyl.

As stated above, aryl phosphines for a heterogeneous catalyst in which phosphine units are incorporated into a polymer chain can also be preferably used. A specific example is a triarylphosphine formed by biding one of the phenyl groups of triphenylphosphine to a polymer chain as shown in the chemical formula below

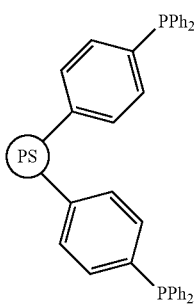

wherein PS represents polystyrene and Ph represents phenyl.

Examples of diamines include tetramethylethylenediamine and 1,2-diphenylethylenediamine.

Of these ligands, phosphines, diamines, and bipyridyls are preferable, triarylphosphines are more preferable, and triphenylphosphine is particularly preferable. The desired compound represented by the formula (1) can typically be obtained at a higher yield when a palladium complex having a bulky ligand, such as phosphines, is used.

Examples of cobalt complexes include $Co_2(CO)_8$; and complexes obtained by combining sodium hydride, sodium alkoxide (e.g., sodium neo-pentoxide, sodium tert-amyloxide, sodium tert-butoxide), cobalt acetate, and carbon monoxide (e.g., CoCRACO).

Examples of nickel complexes include zerovalent nickel complexes; zerovalent nickel complexes generated from divalent nickel complexes during a reaction; and complexes obtained by mixing these nickel complexes with at least one compound (ligand) selected from the group consisting of diketones, phosphines, diamines, and bipyridyls.

Examples of zerovalent nickel complexes include, but are not particularly limited to, $Ni(COD)_2$, $Ni(CDD)_2$ (CDD is cyclodeca-1,5-diene), $Ni(CDT)_2$ (CDT is cyclodeca-1,5,9-trien), $Ni(VCH)_2$ (VCH is 4-vinylcyclohexene), $Ni(CO)_4$, $(PCy_3)_2Ni\!-\!N\!\equiv\!N\!-\!Ni(PCy_3)_2$, and $Ni(PPh_3)_4$.

Examples of divalent nickel complexes include nickel chloride, nickel bromide, nickel acetate, bis(acetylacetonato) nickel(II), and complexes obtained by binding a phosphine ligand, such as triphenyl phosphine, to these complexes. These divalent nickel complexes are, for example, reduced by a reducing species (e.g., phosphines, zinc, and organic metal reagents) that is co-present during a reaction, whereby zerovalent nickel complexes are generated.

The above-described zerovalent nickel complexes or zerovalent nickel complexes generated from divalent nickel complexes through reduction can interact with a ligand that is optionally added during a reaction, and can be converted into zerovalent nickel complexes that are involved in the reaction. It is not always necessary to know how many ligands are bound to a zerovalent nickel complex during the reaction. Preferable nickel complexes for use are those that can highly stabilize the zerovalent nickel complexes generated in a system. Specifically, nickel complexes having a ligand, such as phosphines, diamines, and bipyridyls, are preferable, and nickel complexes having a phosphine are particularly preferable.

Examples of preferable phosphines include trialkylphosphines and triarylphosphines. Specific examples of trialkylphosphines include tri($C_{3-20}$ alkyl)phosphines, such as tricyclohexylphosphine, triisopropylphosphine, tri-t-butylphosphine, trihexylphosphine, triadamantylphosphine, tricyclopentylphosphine, di-t-butylmethylphosphine, tribicyclo[2,2,2]octylphosphine, and trinorbornylphosphine. Examples of triarylphosphines include tri(monocyclic aryl) phosphines, such as triphenylphosphine, trimesitylphosphine, and tri(o-tolyl)phosphine. Of these, triphenylphosphine, tricyclohexylphosphine, tri-t-butylphosphine, and triisopropylphosphine are preferable.

As stated above, aryl phosphines for a heterogeneous catalyst in which phosphine units are incorporated into a polymer chain can also be preferably used. A specific example is a triarylphosphine formed by binding one of the phenyl groups of triphenylphosphine to a polymer chain as shown in the chemical formula below

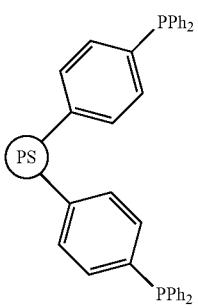

wherein PS represents polystyrene and Ph represents phenyl.

Examples of diamines include tetramethylethylenediamine and 1,2-diphenylethylenediamine.

Of these ligands, preferable are bulky ligands, including triarylphosphines, such as triphenylphosphine and tri(o-tolyl)phosphine; tricyclohexylphosphine; and tri-t-butylphosphine. The desired compound represented by the formula (1) can typically be obtained at a higher yield when a nickel complex having a bulky ligand, such as triarylphosphines, is used.

The transition metal catalyst is preferably an organic palladium complex from the viewpoints of the yield and selectivity of the compound represented by the formula (1).

The transition metal catalyst may be a supported catalyst in which a transition metal is supported by a carrier. Such a supported catalyst has a cost advantage because the catalyst can be recycled. Examples of carriers include carbon, alumina, silica alumina, silica, barium carbonate, barium sulfate, calcium carbonate, titanium oxide, zirconium oxide, and zeolite. Particularly preferable examples of supported catalysts include palladium carbon.

The amount of the transition metal catalyst is typically in the range of 0.002 to 10 moles, preferably in the range of 0.005 to 5 moles, more preferably in the range of 0.005 to 1 mole, and still more preferably in the range of 0.01 to 1 mole, per mole of the compound represented by the formula (2).

Step A is carried out in the presence of a base. Examples of the base used in step (A) include amines, inorganic bases, and organic metal bases. Examples of amines include triethylamine, tri(n-propyl)amine, tri(n-butyl)amine, diisopropylethylamine, cyclohexyldimethylamine, pyridine, lutidine, γ-collidine, N,N-dimethylaniline, N-methylpiperidine, N-methylpyrrolidine, and N-methylmorpholine. Examples of inorganic bases include lithium hydroxide, potassium hydroxide, sodium hydroxide, calcium hydroxide, lithium carbonate, sodium carbonate, potassium carbonate, sodium hydrogen carbonate, and potassium hydrogen carbonate. Examples of organic metal bases include organoalkali metal compounds, such as butyllithium, t-butyllithium, phenyllithium, sodium triphenylmethyl, and ethyl sodium; organic alkaline earth metal compounds, such as methylmagnesium bromide, dimethylmagnesium, phenylmagnesium chloride, phenylcalcium bromide, and bis(dicyclopentadiene)calcium; and alkoxides, such as sodium methoxide and t-butylmethoxide. Preferred examples of bases include lithium hydroxide, triethylamine, potassium carbonate, and lithium carbonate. More preferred examples of bases include triethylamine, potassium carbonate, and lithium carbonate. These bases can be used singly or in a combination of two or more.

The amount of the base is typically in the range of 0.2 to 5 moles, and preferably in the range of about 0.5 to 3 moles, per mole of the compound represented by the formula (2).

The base used in step A preferably comprises (a) an amine and (b) an inorganic base or an organic metal base. The base used in step A more preferably comprises an amine and an inorganic base, and still more preferably consists of an amine and an inorganic base. In a preferred embodiment of the present invention, the base used in step A comprises (a) triethylamine and (b) one or more kinds of inorganic bases selected from the group consisting of lithium hydroxide, potassium carbonate, and lithium carbonate. In a more preferred embodiment of the present invention, the base used in step A consists of (a) triethylamine and (b) one or more kinds of inorganic bases selected from the group consisting of potassium carbonate and lithium carbonate.

The amount of the amine is typically in the range of 0.2 to 5 moles, and preferably in the range of about 0.5 to 3 moles, per mole of the compound represented by the formula (2).

The amount of the inorganic base is in the range of 1 to 10 moles, and preferably in the range of about 2 to 5 moles, per mole of the transition metal catalyst.

Step A is typically carried out at a temperature in the range of 10 to 150° C., preferably in the range 50 to 120° C., more preferably in the range 60 to 110° C., and still more preferably in the range of 60 to 100° C., or 60 to 90° C. When the temperature is excessively low, the starting material conversion and the yield tend to be low. When the temperature is excessively high, analysis performed by the below-described analysis method may suggest the presence of the compound represented by the formula (2), which is a starting material, and by-products or decomposition products in the mixture obtained after the reaction of step A.

Analysis Method

After the reaction, hexafluorobenzene is added as an internal standard with stirring, and the mixture is allowed to stand for a while to thereby precipitate a salt. The supernatant is diluted with deuterochloroform, followed by quantification based on an $^{19}$F-NMR integrated value.

In step A, in addition to the alcohol represented by the formula (3), which can also serve as a solvent, other solvents may also be used. By doing so, the amount of the alcohol represented by the formula (3) for use can be decreased. Examples of solvents include non-aromatic hydrocarbon solvents, such as pentane, hexane, heptane, octane, cyclohexane, decahydronaphthalene, n-decane, isododecane, and tridecane; aromatic hydrocarbon solvents, such as benzene, toluene, xylene, tetralin, veratrole, diethylbenzene, methylnaphthalene, nitrobenzene, o-nitrotoluene, mesitylene, indene, and diphenylsulfide; ketones, such as acetone, methyl ethyl ketone, methyl isobutyl ketone, acetophenone, propiophenone, diisobutyl ketone, and isophorone; halogenated hydrocarbon solvents, such as dichloromethane, chloroform, and chlorobenzene; ether solvents, such as diethylether, tetrahydrofuran, diisopropyl ether, methyl-t-butyl ether, dioxane, dimethoxyethane, diglyme, phenetole, 1,1-dimethoxycyclohexane, and diisoamyl ether; ester solvents, such as ethyl acetate, isopropyl acetate, diethyl malonate, 3-methoxy-3-methylbutyl acetate, γ-butyrolactone, ethylene carbonate, propylene carbonate, dimethyl carbonate, and α-acetyl-γ-butyrolactone; nitrile solvents, such as acetonitrile, and benzonitrile; sulfoxide based solvents, such as dimethyl sulfoxide and sulfolan; and amide solvents, such as N,N-dimethylformamide, N,N-dimethylacetamide, N-methylpyrrolidone, 1,3-dimethyl-2-imidazolidinone, N,N-dimethylacrylamide, N,N-dimethylacetoacetamide, N,N-diethylformamide, and N,N-diethylacetamide.

Preferable examples of solvents include ether solvents, such as diethylether, tetrahydrofuran, diisopropyl ether, methyl-t-butyl ether, dioxane, dimethoxyethane, diglyme, phenetole, 1,1-dimethoxycyclohexane, and diisoamyl ether; and amide solvents, such as N,N-dimethylformamide, N,N- dimethylacetamide, N-methylpyrrolidone, 1,3-dimethyl-2-imidazolidinone, N,N-dimethylacrylamide, N,N-dimethylacetoacetamide, diethylformamide, and N,N-diethylacetamide.

These solvents are preferably inert against the starting materials, catalyst, and products in step A.

Preferably, the solvent for use is an organic solvent having a high boiling point (e.g., 100° C. or more, and more preferably 120° C. or more) for the ease of purifying the compound represented by the formula (1). The use of such an organic solvent enables purification of the compound represented by the formula (1) simply by distillation.

The amount of the solvent for use is not particularly limited as long as a portion or all of the starting materials are dissolved at a reaction temperature. For example, the solvent can be used in an amount of 0.2 to 10 parts by weight, or 0.5 to 10 parts by weight per one part by weight of the compound represented by the formula (2).

The reaction time can be determined, for example, based on the desired starting material conversion, selectivity, and yield. Specifically, the reaction time is, typically, in the range of 1 to 24 hours, and preferably in the range of 2 to 12 hours. The reaction time can be shortened by applying higher reaction temperatures.

The process according to the present invention can achieve a starting material conversion of preferably 90% or more, more preferably 95% or more, and still more preferably 97% or more. The process according to the present invention can achieve a selectivity of the compound represented by the formula (1) of preferably 90% or more, and more preferably 95% or more.

The process according to the present invention can achieve a yield of the compound represented by the formula (1) of preferably 85% or more, and more preferably 90% or more.

The compound represented by the formula (1) obtained by the process according to the present invention may optionally be purified by a known purification method, such as solvent extraction, desiccation, filtration, distillation, concentration, or a combination thereof. Because the process according to the present invention produces by-products and decomposition products in a very small amount, a high-purity compound represented by the formula (1) can be obtained by using a simple method, such as distillation.

EXAMPLES

Hereinafter the Examples describe the present invention in more detail. However, the present invention is not limited to the Examples.

Example 1

0.87 g (6.96 mmol) of 1-bromo-1-fluoroethene, 0.89 g (8.8 mmol) of triethylamine, 0.168 g (0.24 mmol) of dichlorobis(triphenylphosphine)palladium(II), 0.060 g (0.80 mmol) of lithium carbonate, and 10 mL of methanol were placed in a 50-mL stainless-steel autoclave. Carbon monoxide (1.0 MPaG) was introduced thereinto, followed by stirring at 90° C. for 6 hours. After the completion of the reaction, the autoclave was cooled, and the unreacted gas was purged. Subsequently, the autoclave was opened, and 186 mg (1.0 mmol) of hexafluorobenzene was added as an internal standard, followed by stirring. The reaction mixture was allowed to stand for a while, thereby precipitating a salt. The supernatant was diluted with deuterochloroform, followed by quantification based on an $^{19}$F-NMR integrated value, which revealed that 2-fluoroacrylic acid methyl ester (MFA) was present in an amount of 6.31 mmol (yield: 90.7%), and unreacted 1-bromo-1-fluoroethene was present in an amount of 0.19 mmol (recovery: 3.0%). The conversion was 97%. NMR analysis detected four unknown components, and the selectivity of MFA was 94.5%. The table below shows the results.

TABLE 1

|  | Unknown Components | | | | MFA | Starting Materials | HFB (Internal Standard) |
|---|---|---|---|---|---|---|---|
| Chemical Shift (ppm) | −80 | −111 | −116 | −117 | −118 | −62 | −162 |
| NMR Peak Area | 0.03 | 0.18 | 0.07 | 0.09 | 6.31 | 0.19 | 6 |
| Selectivity | 0.4% | 2.7% | 1.0% | 1.3% | 94.5% | | |
| Conversion |  |  |  |  | 97% |  |  |

Example 2

1.02 g (8.18 mmol) of 1-bromo-1-fluoroethene, 0.89 g (8.8 mmol) of triethylamine, 0.168 g (0.24 mmol) of dichlorobis(triphenylphosphine)palladium(II), 0.060 g (0.80 mmol) of lithium carbonate, and 10 mL of methanol were placed in a 50-mL stainless-steel autoclave. Carbon monoxide (1.0 MPaG) was introduced thereinto, followed by stirring at 60° C. for 7 hours. After the completion of the reaction, the autoclave was cooled, and the unreacted gas was purged. Subsequently, the autoclave was opened, and 186 mg (1.0 mmol) of hexafluorobenzene was added as an internal standard, followed by stirring. The reaction mixture was allowed to stand for a while, thereby precipitating a salt. The supernatant was diluted with deuterochloroform, followed by quantification based on an $^{19}$F-NMR integrated value, which revealed that 2-fluoroacrylic acid methyl ester (MFA) was present in an amount of 3.69 mmol (yield: 45%), and unreacted 1-bromo-1-fluoroethene was present in an amount of 4.49 mmol (recovery: 55%). The conversion was 45%, and the selectivity was 100%.

TABLE 2

|  | Unknown Components | | | | MFA | Starting Materials | HFB (Internal Standard) |
|---|---|---|---|---|---|---|---|
| Chemical Shift (ppm) | −80 | −111 | −116 | −117 | −118 | −62 | −162 |
| NMR Peak Area | 0 | 0 | 0 | 0 | 3.69 | 4.49 | 6 |

TABLE 2-continued

|  | Unknown Components | | | | MFA | Starting Materials | HFB (Internal Standard) |
|---|---|---|---|---|---|---|---|
| Selectivity | 0.0% | 0.0% | 0.0% | 0.0% | 100.0% | | |
| Conversion | | | | | 45% | | |

Example 3

0.72 g (5.78 mmol) of 1-bromo-1-fluoroethene, 0.89 g (8.8 mmol) of triethylamine, 0.028 g (0.04 mmol) of dichlorobis(triphenylphosphine)palladium(II), 0.009 g (0.12 mmol) of lithium carbonate, and 10 mL of methanol were placed in a 50-mL stainless-steel autoclave. Carbon monoxide (1.0 MPaG) was introduced thereinto, followed by stirring at 90° C. for 8 hours. After the completion of the reaction, the autoclave was cooled, and the unreacted gas was purged. Subsequently, the autoclave was opened, and 186 mg (1.0 mmol) of hexafluorobenzene was added as an internal standard, followed by stirring. The reaction mixture was allowed to stand for a while, thereby precipitating a salt. The supernatant was diluted with deuterochloroform, followed by quantification based on an $^{19}$F-NMR integrated value, which revealed that 2-fluoroacrylic acid methyl ester (MFA) was present in an amount of 4.6 mmol (yield: 80%), and unreacted 1-bromo-1-fluoroethene was present in an amount of 0.94 mmol (recovery: 16%). The conversion was 83%. NMR analysis detected one unknown component, and the selectivity was 95%.

TABLE 3

|  | Unknown Components | | | | MFA | Starting Materials | HFB (Internal Standard) |
|---|---|---|---|---|---|---|---|
| Chemical Shift (ppm) | −80 | −111 | −116 | −117 | −118 | −62 | −162 |
| NMR Peak Area | 0 | 0.24 | 0 | 0 | 4.6 | 0.94 | 6 |
| Selectivity | 0.0% | 5.0% | 0.0% | 0.0% | 95.0% | | |
| Conversion | | | | | 83% | | |

Example 4

1.06 g (8.48 mmol) of 1-bromo-1-fluoroethene, 0.97 g (9.6 mmol) of triethylamine, 59.1 mg (0.08 mmol) of dichlorobis(tricyclohexylphosphine)palladium(II), and 8 mL of methanol were placed in a 50-mL stainless-steel autoclave. Carbon monoxide (1.0 MPaG) was introduced thereinto, followed by stirring at 100° C. for 9 hours. After the completion of the reaction, the autoclave was cooled, and the unreacted gas was purged. Subsequently, the autoclave was opened, and 186 mg (1.0 mmol) of hexafluorobenzene was added as an internal standard, followed by stirring. The reaction mixture was allowed to stand for a while, thereby precipitating a salt. The supernatant was diluted with deuterochloroform, followed by quantification based on an $^{19}$F-NMR integrated value, which revealed that 2-fluoroacrylic acid methyl ester (MFA) was present in an amount of 6.67 mmol (yield: 78.6%), and unreacted 1-bromo-1-fluoroethene was present in an amount of 1.59 mmol (recovery: 18.8%). The conversion was 80.2%.

Example 5

0.98 g (7.84 mmol) of 1-bromo-1-fluoroethene, 0.97 g (9.6 mmol) of triethylamine, 40.9 mg (0.08 mmol) of bis(tri-t-butylphosphine)palladium(0), and 8 mL of methanol were placed in a 50-mL stainless-steel autoclave. Carbon monoxide (1.0 MPaG) was introduced thereinto, followed by stirring at 100° C. for 9 hours. After the completion of the reaction, the autoclave was cooled, and the unreacted gas was purged. Subsequently, the autoclave was opened, and 186 mg (1.0 mmol) of hexafluorobenzene was added as an internal standard, followed by stirring. The reaction mixture was allowed to stand for a while, thereby precipitating a salt. The supernatant was diluted with deuterochloroform, followed by quantification based on an $^{19}$F-NMR integrated value, which revealed that 2-fluoroacrylic acid methyl ester (MFA) was present in an amount of 4.95 mmol (yield: 63.1%), and unreacted 1-bromo-1-fluoroethene was present in an amount of 2.60 mmol (recovery: 33.1%). The conversion was 65.3%.

Example 6

1.12 g (8.96 mmol) of 1-bromo-1-fluoroethene, 0.97 g (9.6 mmol) of triethylamine, 14.2 mg (0.08 mmol) of palladium(II) chloride, 38.1 mg (0.08 mmol) of 2-dicyclohexyl phosphino-2'4'6'-triisopropyl biphenyl, and 8 mL of methanol were placed in a 50-mL stainless-steel autoclave. Carbon monoxide (1.0 MPaG) was introduced thereinto, followed by stirring at 100° C. for 8 hours. After the completion of the reaction, the autoclave was cooled, and the unreacted gas was purged. Subsequently, the autoclave was opened, and 186 mg (1.0 mmol) of hexafluorobenzene was added as an internal standard, followed by stirring. The reaction mixture was allowed to stand for a while, thereby precipitating a salt. The supernatant was diluted with deuterochloroform, followed by quantification based on an $^{19}$F-NMR integrated value, which revealed that 2-fluoroacrylic acid methyl ester (MFA) was present in an amount of 7.64 mmol (yield: 85.3%), and unreacted 1-bromo-1-fluoroethene was present in an amount of 1.08 mmol (recovery: 12.0%). The conversion was 87.5%.

Example 7

0.85 g (6.80 mmol) of 1-bromo-1-fluoroethene, 0.97 g (9.6 mmol) of triethylamine, 5.6 mg (0.008 mmol) of dichlorobis(triphenylphosphine)palladium(II), and 8 mL of methanol were placed in a 50-mL stainless-steel autoclave. Carbon monoxide (1.0 MPaG) was introduced thereinto, followed by stirring at 100° C. for 7 hours. After the completion of the reaction, the autoclave was cooled, and the unreacted gas was purged. Subsequently, the autoclave was opened, and 186 mg (1.0 mmol) of hexafluorobenzene was added as an internal standard, followed by stirring. The reaction mixture was allowed to stand for a while, thereby precipitating a salt. The supernatant was diluted with deuterochloroform, followed by quantification based on an $^{19}$F-NMR integrated value, which revealed that 2-fluoroacrylic acid methyl ester (MFA) was present in an amount of 4.80 mmol (yield: 70.6%), and unreacted 1-bromo-1-fluoroethene was present in an amount of 1.92 mmol (recovery: 28.2%). The conversion was 71.4%.

Example 8

0.93 g (7.44 mmol) of 1-bromo-1-fluoroethene, 0.97 g (9.6 mmol) of triethylamine, 56.2 mg (0.08 mmol) of dichlorobis(triphenylphosphine)palladium(II), and 8 mL of ethanol were placed in a 50-mL stainless-steel autoclave. Carbon monoxide (1.0 MPaG) was introduced thereinto, followed by stirring at 100° C. for 6 hours. After the completion of the reaction, the autoclave was cooled, and the unreacted gas was purged. Subsequently, the autoclave was opened, and 186 mg (1.0 mmol) of hexafluorobenzene was added as an internal standard, followed by stirring. The reaction mixture was allowed to stand for a while, thereby precipitating a salt. The supernatant was diluted with deuterochloroform, followed by quantification based on an $^{19}$F-NMR integrated value, which revealed that 2-fluoroacrylic acid ethyl ester was present in an amount of 6.57 mmol (yield: 88.3%), and unreacted 1-bromo-1-fluoroethene was present in an amount of 0.68 mmol (recovery: 9.2%). The conversion was 90.1%.

Example 9

1.04 g (8.32 mmol) of 1-bromo-1-fluoroethene, 0.97 g (9.6 mmol) of triethylamine, 56.2 mg (0.08 mmol) of dichlorobis(triphenylphosphine)palladium(II), 0.51 g (16.0 mmol) of methanol, and 8 mL of tetrahydrofuran were placed in a 50-mL stainless-steel autoclave. Carbon monoxide (1.0 MPaG) was introduced thereinto, followed by stirring at 100° C. for 6 hours. After the completion of the reaction, the autoclave was cooled, and the unreacted gas was purged. Subsequently, the autoclave was opened, and 186 mg (1.0 mmol) of hexafluorobenzene was added as an internal standard, followed by stirring. The reaction mixture was allowed to stand for a while, thereby precipitating a salt. The supernatant was diluted with deuterochloroform, followed by quantification based on an $^{19}$F-NMR integrated value, which revealed that 2-fluoroacrylic acid methyl ester (MFA) was present in an amount of 7.47 mmol (yield: 89.8%), and unreacted 1-bromo-1-fluoroethene was present in an amount of 0.62 mmol (recovery: 7.4%). The conversion was 91.7%.

Example 10

1.01 g (8.08 mmol) of 1-bromo-1-fluoroethene, 0.97 g (9.6 mmol) of triethylamine, 56.2 mg (0.08 mmol) of dichlorobis(triphenylphosphine)palladium(II), 0.51 g (16.0 mmol) of methanol, and 8 mL of N-methylpyrrolidone were placed in a 50-mL stainless-steel autoclave. Carbon monoxide (1.0 MPaG) was introduced thereinto, followed by stirring at 100° C. for 6 hours. After the completion of the reaction, the autoclave was cooled, and the unreacted gas was purged. Subsequently, the autoclave was opened, and 186 mg (1.0 mmol) of hexafluorobenzene was added as an internal standard, followed by stirring. The reaction mixture was allowed to stand for a while, thereby precipitating a salt. The supernatant was diluted with deuterochloroform, followed by quantification based on an $^{19}$F-NMR integrated value, which revealed that 2-fluoroacrylic acid methyl ester (MFA) was present in an amount of 7.30 mmol (yield: 90.3%), and unreacted 1-bromo-1-fluoroethene was present in an amount of 0.66 mmol (recovery: 8.2%). The conversion was 91.5%.

Example 11

0.97 g (7.76 mmol) of 1-bromo-1-fluoroethene, 0.97 g (9.6 mmol) of triethylamine, 85.1 mg (0.08 mmol) of 10% palladium carbon, 42.0 mg (0.16 mmol) of triphenyl phosphine, and 8 mL of methanol were placed in a 50-mL stainless-steel autoclave. Carbon monoxide (1.0 MPaG) was introduced thereinto, followed by stirring at 100° C. for 6 hours. After the completion of the reaction, the autoclave was cooled, and the unreacted gas was purged. Subsequently, the autoclave was opened, and 186 mg (1.0 mmol) of hexafluorobenzene was added as an internal standard, followed by stirring. The reaction mixture was allowed to stand for a while, thereby precipitating a salt. The supernatant was diluted with deuterochloroform, followed by quantification based on an $^{19}$F-NMR integrated value, which revealed that 2-fluoroacrylic acid methyl ester (MFA) was present in an amount of 5.86 mmol (yield: 75.5%), and unreacted 1-bromo-1-fluoroethene was present in an amount of 0.71 mmol (recovery: 9.2%). The conversion was 87.0%.

Example 12

1.13 g (14.0 mmol) of 1-chloro-1-fluoroethene, 1.38 g (13.7 mmol) of triethylamine, 0.44 g (0.62 mmol) of dichlorobis[di-t-butyl(p-dimethylaminophenyl)phosphino]palladium(II), and 6.2 mL of methanol were placed in a 50-mL stainless-steel autoclave. Carbon monoxide (0.7 MPaG) was introduced thereinto, followed by stirring at 100° C. for 13 hours. After the completion of the reaction, the autoclave was cooled, and the unreacted gas was purged. Subsequently, the autoclave was opened, and 186 mg (1.0 mmol) of hexafluorobenzene was added as an internal standard, followed by stirring. The reaction mixture was allowed to stand for a while, thereby precipitating a salt. The supernatant was diluted with deuterochloroform, followed by quantification based on an $^{19}$F-NMR integrated value, which revealed that 2-fluoroacrylic acid methyl ester (MFA) was present in an amount of 5.98 mmol (yield: 42.7%), and an unreacted 1-chloro-1-fluoroethene was present in an amount of 5.07 mmol (recovery: 36.2%). The conversion was 63.0%.

Example 13

0.92 g (11.4 mmol) of 1-chloro-1-fluoroethene, 1.38 g (13.7 mmol) of triethylamine, 0.40 g (0.62 mmol) of bis(tri-t-butylphosphine)palladium(0), and 6.2 mL of methanol were placed in a 50-mL stainless-steel autoclave. Carbon monoxide (0.7 MPaG) was introduced thereinto, followed by stirring at 100° C. for 18 hours. After the completion of the reaction, the autoclave was cooled, and the unreacted gas was purged. Subsequently, the autoclave was opened, and 186 mg (1.0 mmol) of hexafluorobenzene was added as an internal standard, followed by stirring. The reaction mixture was allowed to stand for a while, thereby precipitating a salt. The supernatant was diluted with deuterochloroform, followed by quantification based on an $^{19}$F-NMR integrated value, which revealed that 2-fluoroacrylic acid methyl ester (MFA) was present in an amount of 8.82 mmol (yield: 77.4%), and unreacted 1-chloro-1-fluoroethene was present in an amount of 1.89 mmol (recovery: 16.6%). The conversion was 81.3%.

Example 14

0.99 g (12.3 mmol) of 1-chloro-1-fluoroethene, 1.38 g (13.7 mmol) of triethylamine, 0.46 g (0.62 mmol) of dichlorobis(tricyclohexylphosphine)palladium (II), and 6.2 mL of methanol were placed in a 50-mL stainless-steel autoclave. Carbon monoxide (0.7 MPaG) was introduced thereinto, followed by stirring at 100° C. for 10 hours. After the completion of the reaction, the autoclave was cooled, and the unreacted gas was purged. Subsequently, the autoclave was opened, and 186 mg (1.0 mmol) of hexafluorobenzene was added as an internal standard, followed by stirring. The reaction mixture was allowed to stand for a while, thereby precipitating a salt. The supernatant was diluted with deuterochloroform, followed by quantification based on an $^{19}$F-NMR integrated value, which revealed that 2-fluoroacrylic acid methyl ester (MFA) was present in an amount of 2.80 mmol (yield: 22.8%), and unreacted 1-chloro-1-fluoroethene was present in an amount of 6.82 mmol (recovery: 55.4%). The conversion was 39.0%.

Example 15

1.05 g (13.0 mmol) of 1-chloro-1-fluoroethene, 1.38 g (13.7 mmol) of triethylamine, 0.11 g (0.62 mmol) of palladium chloride, 0.60 g (1.24 mmol) of 2-dicyclohexyl phosphino-2',4',6'-triisopropyl biphenyl, and 6.2 mL of methanol were placed in a 50-mL stainless-steel autoclave. Carbon monoxide (0.7 MPaG) was introduced thereinto, followed by stirring at 100° C. for 12 hours. After the completion of the reaction, the autoclave was cooled, and the unreacted gas was purged. Subsequently, the autoclave was opened, and 186 mg (1.0 mmol) of hexafluorobenzene was added as an internal standard, followed by stirring. The reaction mixture was allowed to stand for a while, thereby precipitating a salt. The supernatant was diluted with deuterochloroform, followed by quantification based on an $^{19}$F-NMR integrated value, which revealed that 2-fluoroacrylic acid methyl ester (MFA) was present in an amount of 1.04 mmol (yield: 8.0%), and unreacted 1-chloro-1-fluoroethene was present in an amount of 9.18 mmol (recovery: 70.6%). The conversion was 20.7%.

Example 16

0.93 g (11.6 mmol) of 1-chloro-1-fluoroethene, 1.38 g (13.7 mmol) of triethylamine, 47.0 mg (0.06 mmol) of dichloro[4,5-bis(diphenylphosphino)-9,9'-dimethylxanthene]palladium(II), and 6.2 mL of methanol were placed in a 50-mL stainless-steel autoclave. Carbon monoxide (0.7 MPaG) was introduced thereinto, followed by stirring at 100° C. for 20 hours. After the completion of the reaction, the autoclave was cooled, and the unreacted gas was purged. Subsequently, the autoclave was opened, and 186 mg (1.0 mmol) of hexafluorobenzene was added as an internal standard, followed by stirring. The reaction mixture was allowed to stand for a while, thereby precipitating a salt. The supernatant was diluted with deuterochloroform, followed by quantification based on an $^{19}$F-NMR integrated value, which revealed that 2-fluoroacrylic acid methyl ester (MFA) was present in an amount of 2.19 mmol (yield: 18.9%), and unreacted 1-chloro-1-fluoroethene was present in an amount of 7.98 mmol (recovery: 68.8%). The conversion was 20.0%.

Example 17

1.03 g (12.8 mmol) of 1-chloro-1-fluoroethene, 1.38 g (13.7 mmol) of triethylamine, 11.0 mg (0.06 mmol) of palladium chloride, 11.0 mg (0.06 mmol) of 1,3-bis(diphenylphosphino)propane, and 6.2 mL of methanol were placed in a 50-mL stainless-steel autoclave. Carbon monoxide (0.7 MPaG) was introduced thereinto, followed by stirring at 100° C. for 19 hours. After the completion of the reaction, the autoclave was cooled, and the unreacted gas was purged. Subsequently, the autoclave was opened, and 186 mg (1.0 mmol) of hexafluorobenzene was added as an internal standard, followed by stirring. The reaction mixture was allowed to stand for a while, thereby precipitating a salt. The supernatant was diluted with deuterochloroform, followed by quantification based on an $^{19}$F-NMR integrated value, which revealed that 2-fluoroacrylic acid methyl ester (MFA) was present in an amount of 6.42 mmol (yield: 50.2%), and unreacted 1-chloro-1-fluoroethene was present in an amount of 5.15 mmol (recovery: 40.2%). The conversion was 57.1%.

Example 18

1.01 g (12.54 mmol) of 1-chloro-1-fluoroethene, 1.38 g (13.7 mmol) of triethylamine, 11.0 mg (0.06 mmol) of palladium chloride, 38.7 mg (0.06 mmol) of 2,2'-bis(diphenylphosphino)-1,1'-binaphthyl, and 6.2 mL of methanol were placed in a 50-mL stainless-steel autoclave. Carbon monoxide (0.7 MPaG) was introduced thereinto, followed by stirring at 100° C. for 14 hours. After the completion of the reaction, the autoclave was cooled, and the unreacted gas was purged. Subsequently, the autoclave was opened, and 186 mg (1.0 mmol) of hexafluorobenzene was added as an internal standard, followed by stirring. The reaction mixture was allowed to stand for a while, thereby precipitating a salt. The supernatant was diluted with deuterochloroform, followed by quantification based on an $^{19}$F-NMR integrated value, which revealed that 2-fluoroacrylic acid methyl ester (MFA) was present in an amount of 6.16 mmol (yield: 49.1%), and unreacted 1-chloro-1-fluoroethene was present in an amount of 4.89 mmol (recovery: 39.0%). The conversion was 51.8%.

INDUSTRIAL APPLICABILITY

The present invention enables the production of α-fluoroacrylic acid ester useful as a synthetic intermediate at a high starting material conversion, high selectivity, and high yield.

The invention claimed is:
1. A process for producing a compound represented by the formula (1)

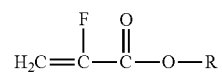

(1)

wherein R represents alkyl optionally substituted with one or more fluorine atoms,
the process comprising reacting a compound represented by the formula (2)

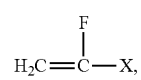

(2)

wherein X represents a bromine atom or a chlorine atom, with an alcohol represented by the formula (3)

(3)

wherein R is as defined above, and carbon monoxide in the presence of a transition metal catalyst and a base, at a temperature ranging from 60 to 120° C., to thereby obtain the compound represented by the formula (1).

2. The process according to claim 1, wherein the transition metal catalyst is a palladium catalyst.

3. The process according to claim 1, wherein the base comprises (a) an amine and (b) an inorganic base or an organic metal base.

4. The process according to claim 2, wherein the base comprises (a) an amine and (b) an inorganic base or an organic metal base.

* * * * *